United States Patent
Keil

(10) Patent No.: US 10,242,465 B2
(45) Date of Patent: Mar. 26, 2019

(54) METHOD FOR DETERMINING A PROJECTION DATA SET, PROJECTION-DETERMINING SYSTEM, COMPUTER PROGRAM PRODUCT AND COMPUTER-READABLE STORAGE MEDIUM

(71) Applicant: Siemens Healthcare GmbH, Erlangen (DE)

(72) Inventor: Miriam Keil, Erlangen-Dechsendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/900,944

(22) Filed: Feb. 21, 2018

(65) Prior Publication Data

US 2018/0247433 A1    Aug. 30, 2018

(30) Foreign Application Priority Data

Feb. 24, 2017    (DE) .................. 10 2017 203 048

(51) Int. Cl.
*G06K 9/00* (2006.01)
*G06T 11/00* (2006.01)
(Continued)

(52) U.S. Cl.
CPC .......... *G06T 11/003* (2013.01); *A61B 5/0033* (2013.01); *A61B 5/055* (2013.01);
(Continued)

(58) Field of Classification Search
None
See application file for complete search history.

(56) References Cited

U.S. PATENT DOCUMENTS

2007/0165930 A1* 7/2007 Feuerlein ............. G06T 1/60
382/128
2008/0019581 A1* 1/2008 Gkanatsios ............ A61B 6/025
382/131

(Continued)

FOREIGN PATENT DOCUMENTS

DE    102007026520 A1    12/2008
DE    102008052690 A1    4/2010

OTHER PUBLICATIONS

German Office Action, Application No. 10 201 7 203 048.8, dated Nov. 16, 2018.
(Continued)

*Primary Examiner* — Hadi Akhavannik
(74) *Attorney, Agent, or Firm* — Harness, Dickey & Pierce, P.L.C.

(57) ABSTRACT

A raw data set is acquired using a scan protocol via an imaging medical device. In an embodiment of a method, the raw data set and the scan protocol are transmitted from the medical device to a reconstruction unit. Furthermore, an at least two-dimensional image data set is calculated from the raw data set via the reconstruction unit. Furthermore, a display parameter is fetched via the reconstruction unit, the display parameter being assigned to the scan protocol and the display parameter defining a first projection method for the image data set. Furthermore, the image data set and the display parameter are transmitted from the reconstruction unit to a display unit, the reconstruction unit and the display unit being spatially separate. Furthermore, a first projection data set is determined by applying the first projection method to the image data set via the display unit.

23 Claims, 4 Drawing Sheets

(51) Int. Cl.
  *A61B 5/055*   (2006.01)
  *G06F 19/00*   (2018.01)
  *A61B 90/00*   (2016.01)
  *A61B 5/00*    (2006.01)
  *G16H 30/20*   (2018.01)
  *G09G 5/00*    (2006.01)

(52) U.S. Cl.
  CPC .............. *A61B 90/00* (2016.02); *G06F 19/00* (2013.01); *G06T 11/00* (2013.01); *G09G 5/005* (2013.01); *G16H 30/20* (2018.01); *G06T 2210/41* (2013.01); *G09G 2380/08* (2013.01)

(56) References Cited

U.S. PATENT DOCUMENTS

| | | | |
|---|---|---|---|
| 2008/0310698 A1 | 12/2008 | Boeing et al. | |
| 2010/0097378 A1 | 4/2010 | Barth et al. | |
| 2011/0214055 A1* | 9/2011 | Georgiev | G06F 19/00 715/702 |
| 2014/0177803 A1* | 6/2014 | Stevens | A61B 6/52 378/98 |
| 2015/0279059 A1* | 10/2015 | Barski | G06T 15/205 345/427 |

OTHER PUBLICATIONS

German Decision to Grant a Patent, Application No. 10 2017 203 048.8, dated Nov. 28, 2017.

\* cited by examiner

METHOD FOR DETERMINING A PROJECTION DATA SET, PROJECTION-DETERMINING SYSTEM, COMPUTER PROGRAM PRODUCT AND COMPUTER-READABLE STORAGE MEDIUM

PRIORITY STATEMENT

The present application hereby claims priority under 35 U.S.C. § 119 to German patent application number DE 102017203048.8 filed Feb. 24, 2017, the entire contents of which are hereby incorporated herein by reference.

FIELD

At least one embodiment of the invention relates generally to a method for determining a projection data set and/or a projection determining system.

BACKGROUND

In medical imaging, in particular in tomographic medical imaging, typically the raw data acquired by the imaging device is converted by a reconstruction unit into image data and stored in a standardized format. This image data can then be viewed and evaluated by a user.

Herein, different representations of the target volume examined are used for different medical issues. In particular for special examinations, for example angiography or magnetic resonance cholangiopancreatography ("MRCP" for short), the image data has to be reformatted before viewing or depicted in some other way. Inter alia, multiplanar reconstructions ("MPR" for short), maximum intensity projections ("MIP" for short) or subtractions are used for this purpose.

It is known to implement the different representations in the software of the reconstruction unit. However, for this, the reconstruction unit software has to be subject to complex and expensive changes on each new or changed representation.

SUMMARY

The inventors have discovered that if the user requires other representations for the diagnosis, the image data has to be time-consumingly reconstructed again or it is even necessary re-acquire raw data. At least one embodiment of the present therefore provides a solution enabling a more flexible and cost-effective way of calculating different representations of the examination volume for the user.

At least one embodiment of the invention is directed to a method, a projection-determining system, a computer program product and/or a computer-readable storage medium. Advantageous developments are described in the claims.

Features, advantages or alternative embodiments mentioned may also be transferred to the other claimed subject matter and vice versa. In other words, the substantive claims (which are, for example, directed at a device) can also be developed with the features described or claimed in connection with a method. Herein, the corresponding functional features of the method are embodied by corresponding substantive modules.

At least one embodiment of the invention is directed to a method for determining a projection data set comprising the following method steps:

acquisition (ACQ) of a raw data set using a scan protocol (300) via an imaging medical device (200), first transmission (TRM-1) of the raw data set and the scan protocol (300) from the imaging medical device (200) to a reconstruction unit (220), calculation (CALC) of an at least two-dimensional image data set (400) from the raw data set via the reconstruction unit (220), fetching (FET) of a display parameter (320) via the reconstruction unit (220), wherein the display parameter (320) is assigned to the scan protocol (300), and wherein the display parameter (320) defines a first projection method (330) for the image data set, second transmission (TRM-2) of the image data set (400) and the display parameter (320) from the reconstruction unit (220) to a display unit (240), wherein the reconstruction unit (220) and the display unit (240) are spatially separate, first determination (DET-1) of a first projection data set (500) by applying the first projection method (330) to the image data set (400) via the display unit (240).

At least one embodiment of the invention furthermore relates a projection-determining system for determining a projection data set comprising:

an imaging medical device, embodied to acquire a raw data set using a scan protocol, furthermore embodied for the first transmission of the raw data set and the scan protocol from the medical device to a reconstruction unit, a reconstruction unit, embodied for the calculation of an at least two-dimensional image data set from the raw data set, furthermore embodied to fetch a display parameter, wherein the display parameter is assigned to the scan protocol, and wherein the display parameter defines a first projection method for the image data set, furthermore embodied for the second transmission of the image data set and the display parameter to a display unit, a display unit, spatially separate from the reconstruction unit, embodied for the first determination of a first projection data set by applying the first projection method to the image data set.

At least one embodiment of the invention also relates to a projection-determining system. A projection-determining system of this kind can in particular be embodied to carry out the above-described methods according to the method and the aspects thereof. The projection-determining system is embodied to carry out these methods and the embodiments thereof in that the imaging medical device, the reconstruction unit and the display unit are embodied to carry out the corresponding method steps. The reconstruction unit and the display unit are in particular embodied to carry out the corresponding method steps in that the respective interfaces and computing units are embodied to carry out the corresponding method steps.

At least one embodiment of the invention also relates to a computer program product with a computer program and a computer-readable medium. An extensively software-based implementation has the advantage that it is also possible to retrofit projection-determining systems used to date in a simple way via a software update in order to work in the manner according to the invention. In addition to the computer program, a computer program product optionally comprises additional parts, such as, for example documentation and/or additional components and hardware components, such as, for example, hardware keys (dongles etc.) for using the software.

BRIEF DESCRIPTION OF THE DRAWINGS

The following describes and explains the invention in more detail with reference to the example embodiments shown in the figures.

DETAILED DESCRIPTION OF THE EXAMPLE EMBODIMENTS

Figure 1:
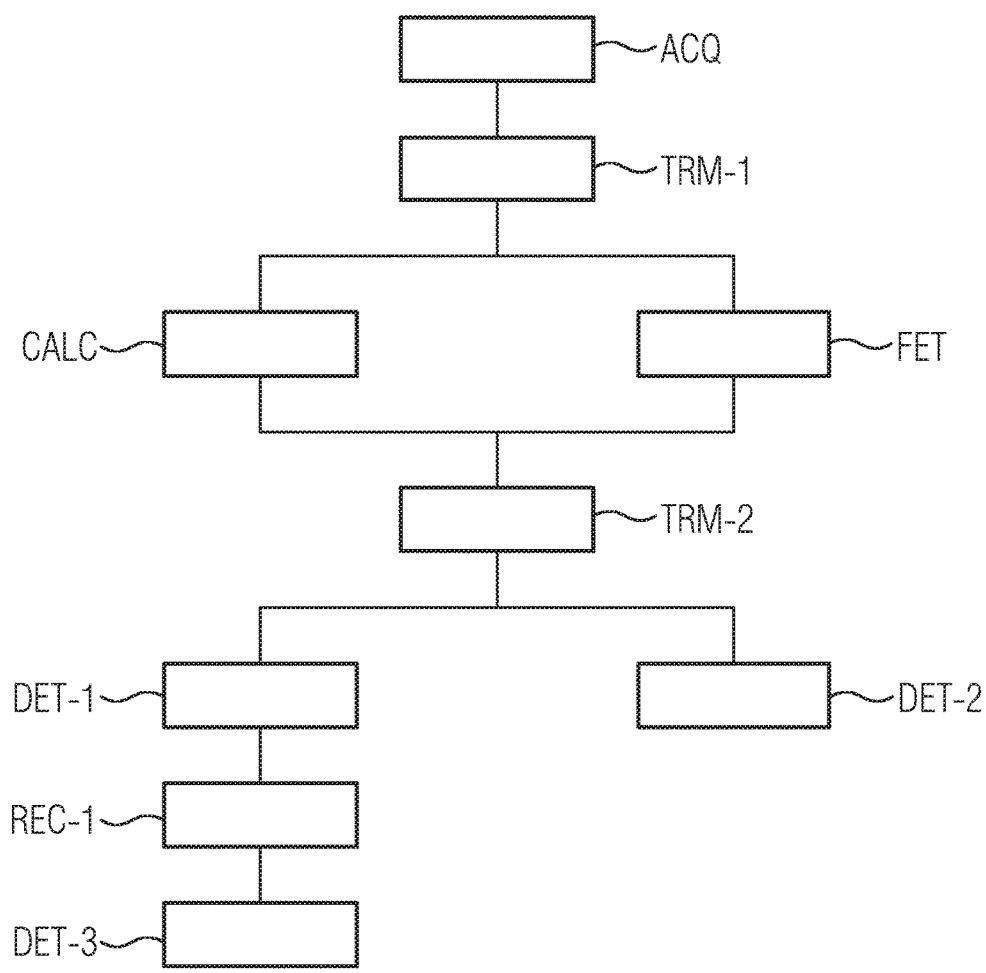
FIG. 1 shows a flow diagram of an example embodiment of the method according to the method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is based on the principle that a raw data set is acquired using a scan protocol by way of an imaging medical device. The raw data set can in particular relate to an examination volume. Furthermore, the raw data set and the scan protocol are transmitted from the medical device to a reconstruction unit. This first transmission in performed in particular at an input interface of the reconstruction unit.

Furthermore, an at least two-dimensional image data set is calculated from the raw data set via the reconstruction unit. The calculation is performed in particular via a computing unit of the reconstruction unit.

Furthermore, a display parameter is fetched via the reconstruction unit, wherein the display parameter is assigned to the scan protocol and wherein the display parameter defines a first projection method for the image data set. The fetching is performed in particular via the computing unit of the reconstruction unit.

Furthermore, the image data set and the display parameter are transmitted from the reconstruction unit to a display unit, wherein the reconstruction unit and the display unit are spatially separate. This second transmission is performed in particular from an output interface of the reconstruction unit to an interface of the display unit.

Furthermore, a first projection data set is determined by applying the first projection method to the image data set via the display unit. The determination is performed in particular via a computing unit of the display unit.

A reconstruction unit and a display unit are in particular spatially separate if they are not jointly integrated in another unit but are only connected to one another for communication, for example wirelessly or via a cable connection. In particular, the reconstruction unit and the display unit are embodied separately. In other words, the reconstruction unit and the display unit are different units. The reconstruction unit and the display unit can in particular be arranged in two different rooms although they can also be arranged in a common room.

The inventors have recognized that this kind of communication between the reconstruction unit and the display unit enables different projection methods to be used particularly quickly and flexibly for an image data set. Since in particular the calculation of the reconstruction is separate from the calculation of a projection, the reconstruction or the reconstruction unit is not affected by changes to the display unit or to the different projection methods. The assignment of a display parameter to a scan protocol enables a standard projection method to be assigned to scan protocol as a result which the method can be sped up since it is not necessary to first wait for a scan protocol to be input by a user. Furthermore, this enables, for example, the definition of different standard projection methods for different users.

According to a further embodiment of the invention, the scan protocol comprises the display parameter; furthermore, the fetching is performed by extraction of the display parameter from the scan protocol. The inventors have recognized that it is possible to establish an assignment between the display parameter and the scan protocol in a particularly simple and cost-effective way if the display parameter is contained directly in the protocol.

According to a further embodiment of the invention, the fetching is based on a database, wherein the database comprises pairs of reference scan protocols and reference display parameters. Herein, the display parameter is the reference display parameter for which the associated reference scan protocol corresponds to the scan protocol. Herein, a scan protocol in particular corresponds to a reference scan protocol if the scan protocol and the reference scan protocol are identical. A scan protocol can also correspond to a reference scan protocol if some or all of the parameters of the protocols are similar. Two parameters are similar if their relative deviation lies within a predefined region. A scan protocol and/or a reference scan protocol can in particular be identified and compared by a unique identification number. The inventors have recognized that this kind of database means that no cost-intensive changes to existing scan protocols are necessary. Furthermore, the use of different databases enables the standard projection method and hence the method to be better adapted to the respective user; furthermore, this makes it very easy to use self-learning methods.

According to a further embodiment of the invention, the display parameter furthermore defines a second projection method for the image data set. Furthermore, a second projection data set is determined by applying the second projection method to the image data set via the display unit. Herein, the determination is performed in particular via a computing unit of the display unit. The inventors have recognized that the definition of a second projection method in the display parameter enables two different projection data sets of the same image data set to be calculated. This means it is in particular not necessary to transmit the image data set several times between the reconstruction unit and the display unit; furthermore, it is also not necessary to calculate a second image data set.

According to a further embodiment of the invention, furthermore a changed display parameter is received via the display unit, wherein the changed display parameter defines a changed first projection method for the image data set. Herein, the reception is in particular performed via an input unit of the display unit. Furthermore, a changed first projection data set is determined by applying the changed first projection method to the image data set via the display unit. Herein, the determination is in particular performed via a computing unit of the display unit. The inventors have recognized that changing of the display parameter on the display unit enables the projection method and the projection data set to be changed in a very simple and cost-efficient way. In particular, this does not require data to be exchanged between the reconstruction unit and the display unit. Neither is it necessary to reconstruct the image data set again or to acquire new raw data.

According to a further embodiment of the invention, a reset instruction is received via the display unit. Herein, the reception is in particular performed via an input unit of the display unit. Furthermore, the first projection data set is displayed via the display unit. Herein, the display is in particular performed via an output unit of the display unit. The inventors have recognized that these steps enable a return to the standard projection method in a particularly simple and quick manner. This enables the rapid correction of faulty or unintentional user inputs.

According to a further embodiment of the invention, the image data set comprises DICOM data. The inventors have recognized that the use of DICOM data enables existing projection methods to be applied to this method in a particularly quick and cost-efficient way.

According to a further embodiment of the invention, the first projection data set is a two-dimensional representation of the image data set or a temporal sequence of two-dimensional representations of the image data set. In particular, the second projection data set and/or the changed first projection data set are also a two-dimensional representation of the image data set or a temporal sequence of two-dimensional representations of the image data set. The inventors have recognized that a two-dimensional representation can be depicted particularly quickly on a display unit.

According to a further embodiment of the invention, the first projection method and/or the second projection method comprise at least one projection type and one projection direction. The projection type is in particular the type of the projection used. The inventors have recognized that the projection type and the projection direction enable the projection data set to be displayed to be described particularly simply and with little memory utilization.

According to a further embodiment of the invention, the projection type corresponds to a slice display, a maximum intensity projection, a multiplanar reconstruction, a volume rendering or a subtraction projection. Furthermore, the projection type can also be a compilation of several acquisitions of different subregions of the examination region. The inventors have recognized that these projection types are suitable for medical and/or diagnostic imaging particularly.

According to a further embodiment of the invention, the first projection method and/or the second projection method comprises a rule for mapping intensity values of the image data set on gray and/or color tones of the representation of the first projection data set and/or the representation of the second projection data set. Herein, the first projection method in particular comprises a rule for mapping intensity values of the image data set on gray and/or color tones of the representation of the first projection data set. In particular, the second projection method comprises a rule for mapping intensity values of the image data set on gray and/or color tones of the representation of the second projection data set. The inventors have recognized that a suitable specification of the mapping rule enables the method to be sped up since the mapping rule does not then have to be time-consumingly determined or input by a user.

At least one embodiment of the invention furthermore relates a projection-determining system for determining a projection data set comprising:
an imaging medical device,
embodied to acquire a raw data set using a scan protocol,
furthermore embodied for the first transmission of the raw data set and the scan protocol from the medical device to a reconstruction unit,
a reconstruction unit,
embodied for the calculation of an at least two-dimensional image data set from the raw data set,
furthermore embodied to fetch a display parameter, wherein the display parameter is assigned to the scan protocol, and wherein the display parameter defines a first projection method for the image data set,
furthermore embodied for the second transmission of the image data set and the display parameter to a display unit,
a display unit, spatially separate from the reconstruction unit, embodied for the first determination of a first projection data set by applying the first projection method to the image data set.

The reconstruction unit can in particular comprises an input interface embodied for the first transmission, an output interface embodied for the second transmission and a computing unit embodied for the calculation and the fetching. The reconstruction unit can in particular comprise an interface embodied for the calculation and the fetching and a computing unit embodied for the first determination.

At least one embodiment of the invention also relates to a projection-determining system. A projection-determining system of this kind can in particular be embodied to carry out the above-described methods according to the method and the aspects thereof. The projection-determining system is embodied to carry out these methods and the embodiments thereof in that the imaging medical device, the reconstruction unit and the display unit are embodied to carry out the corresponding method steps. The reconstruction unit and the display unit are in particular embodied to carry out the corresponding method steps in that the respective interfaces and computing units are embodied to carry out the corresponding method steps.

At least one embodiment of the invention also relates to a computer program product with a computer program and a computer-readable medium. An extensively software-based implementation has the advantage that it is also possible to retrofit projection-determining systems used to date in a simple way via a software update in order to work in the manner according to the invention. In addition to the computer program, a computer program product optionally comprises additional parts, such as, for example documentation and/or additional components and hardware components, such as, for example, hardware keys (dongles etc.) for using the software.

A raw data set is an in particular digital data set comprising the scan results from one or more acquisitions by the imaging medical device. Herein, the raw data set can in particular comprise scan values from emitters (for example position, emission power, emission direction, emission characteristics of, for example, X-ray sources or electromagnetic antennas) and detectors (for example intensities in receiving local coils or X-ray detectors); these scan values can in particular also be time-resolved.

An image data set is in particular an at least two-dimensional image data set. An image data set is in particular an at least three-dimensional image data set. An image data set is in particular a three-dimensional image data set or a four-dimensional image data set. An image data set comprises a plurality of pixels and/or voxels. An intensity value can be assigned to each of the pixels and/or voxels. The intensity values can relate to physical, biological and/or chemical properties of the target volume.

A projection data set is in particular a data set that can be derived from the image data set and that can be displayed via an output unit, wherein the output unit is embodied to output at least two-dimensional images, in particular to output two-dimensional images or in particular to output a temporal sequence of two-dimensional images.

A projection method is in particular a rule, in particular a mapping rule that maps the at least two-dimensional image data set on a projection data set. A projection method can comprise a projection type, wherein the projection type can indicate the mapping rule used. A projection method can furthermore comprise a projection direction indicating a preferred direction of projection and can be a parameter of the mapping rule used.

The first step of the example embodiment depicted in FIG. 1 is the acquisition ACQ of a raw data set using a scan protocol 300 via an imaging medical device 200. In this example embodiment, the imaging medical device 200 is a magnetic resonance tomography system. However, alternatively, it can also be a computed tomography system or a positron emission tomography system. The mode of operation of the acquisition ACQ of a raw data set via an imaging medical device 200 is known from the prior art and is therefore not explained in any more detail here.

Herein, the scan protocol 300 comprises the parameters 301, 302, 303, which are set for the acquisition ACQ of the raw data set at the imaging medical device 200. For example, the scan protocol inter alia comprises a unique descriptor 301 of the scan protocol, a designation of the examined body part 302 and the slice thickness 303 of a tomographic acquisition. Furthermore, the scan protocol can specify further parameters, in particular the magnetic field strengths to use and the sequences to use.

The next step in the example embodiment depicted is the first transmission TRM-1 of the raw data set and the scan protocol 300 from the imaging medical device 200 to a reconstruction unit 220. Herein, the raw data set and the scan protocol 300 are received by an input interface 221.1 of the reconstruction unit 220. In the example embodiment depicted, the raw data set is further processed directly via the reconstruction unit 220, however, it is also possible for the raw data set to be stored temporally in a memory unit 223 of the reconstruction unit 220.

In the example embodiment depicted, the first transmission TRM-1 is performed via a cable connection between the imaging medical device 200 and the reconstruction unit 220. The first transmission TRM-1 can also be performed wirelessly. The first transmission TRM-1 can in particular be performed via a computer network, in particular via a local computer network. It is also possible for the reconstruction unit 220 to be part of the imaging medical device 200.

The next step in the example embodiment depicted is the calculation CALC of an at least two-dimensional image data set 400 from the raw data set via the reconstruction unit 220. Herein, the calculation CALC is performed via the computing unit 222 of the reconstruction unit 220. Reconstruction methods known from the prior art for the respective imaging medical device 200 are used for this. For example, reconstruction methods known for imaging via a magnetic resonance tomography system are back projection and Fourier reconstruction. In this example embodiment, the result is a three-dimensional image data set 400 comprising a plurality of voxels, wherein an intensity value is assigned to each voxel. This three-dimensional image data set 400 is a three-dimensional representation of the depicted target volume in a patient.

The next step in the example embodiment depicted is the fetching FET of a display parameter 320 via the reconstruction unit 220, in particular via a computing unit 222 of the reconstruction unit 220, wherein the display parameter 320 is assigned to the scan protocol 300 and wherein the display parameter 320 defines a first projection method 330 for the image data set 400. In the example embodiment depicted, the scan protocol 300 comprises the display parameter 320. Therefore, the display parameter can be extracted directly from the scan protocol 300 via the computing unit 222 of the reconstruction unit 220.

Alternatively, it is also possible for the reconstruction unit 220 to have access to a database 260, which is, for example, stored in the memory unit 223 of the reconstruction unit 220. Alternatively, the database can also be embodied separately from the reconstruction unit, in particular the database can be stored in a central server. Stored in the database 260 are key-value pairs in the form of reference scan protocols 261.1, 261.2 and assigned reference display parameters 262.1, 262.2. In this alternative, the fetching FET is performed in that a search is performed in the database 260 for the reference scan protocol 261.1, 261.2 corresponding to the scan protocol 300. Herein, a scan protocol 300 and a reference scan protocol 261.1, 261.2 correspond if they are identical. The identity can in particular be established via the descriptor 301 of the scan protocol 300 and a descriptor of one of the reference scan protocols 261.1, 261.2.

In the example embodiment depicted, the display parameter 320 defines a first projection method 330 with a first projection type 331 and a first projection direction 332. Here, the first projection type 331 is a maximum intensity projection and, here, the first projection direction 332 the projection direction associated with the maximum intensity projection. Furthermore, the first projection method 330 of the display parameter 320 defines an assignment between the intensity values of the voxels in the image data set 400 and/or the intensity values of the pixels in the first projection data set 500 and the gray tones in the representation of the first projection data set 500. In the example embodiment depicted, the display parameter 320 furthermore comprises a second projection method 340. The second projection method 340 is optional, the existence of a second projection method 340 in the display parameter can in particular depend on the scan protocol 300 assigned to the display parameter 320.

The calculation CALC of the image data set 400 and the fetching FET of the display parameter 320 are independent of one another, therefore it is possible both for the calculation CALC to be performed before the fetching FET and for the fetching FET to be performed before the calculation CALC. It is also possible for the calculation CALC and the fetching FET to take place at least partially simultaneously.

The next step of the example embodiment depicted is the second transmission TRM-2 of the image data set 400 and the display parameter 320 from the reconstruction unit 220 to a display unit 240, wherein the reconstruction unit and the display unit 240 are spatially separate. Herein, the second transmission TRM-2 is performed from an output interface 221.2 of the reconstruction unit 220 to an interface 241 of the display unit 240. In the example embodiment depicted, the reconstruction unit 220 and the display unit 240 are located in separate rooms. Herein, the reconstruction unit 220 is arranged in the immediate vicinity of the imaging medical device 200, but alternatively the reconstruction unit 220 can also be embodied as part of the imaging medical device 200. The display unit 240 is located in a diagnostics room.

The next step of the example embodiment depicted is the first determination DET-1 of a first projection data set 500 by applying the first projection method 330 to the image data set 400 via the display unit 240. Herein, the first determination DET-1 is in particular performed via the computing unit 242 of the display unit 240. Herein, when maximum intensity projection is used as the first projection method 330, parallel beams through the image data set are calculated. The parallel beams then correspond to the pixels in the first projection data set 500. Herein, the intensity in pixels corresponds to the maximum intensity of a voxel intersected by the respective beam.

The example embodiment depicted comprises as a further optional step the second determination DET-2 of a second projection data set 510 by applying the second projection method 340 to the image data set 400 via the display unit 240. Herein, the second determination DET-2 is in particular performed via the computing unit 242 of the display unit 240. This optional second determination DET-2 corresponds to the first determination DET-1, wherein, however, the second projection method 340 can be different from the first projection method 330 and hence in particular the second projection data set 510 can be different from the first projection data set 500. The second projection method 340 is in particular different from the first projection method 330 when the second projection type 341 of the second projection method 340 is different from the first projection type 331 of the first projection method 330. The second projection method 340 is furthermore in particular different from the first projection method 330 when the second projection direction 342 of the second projection method 340 is different from the first projection direction 332 of the first projection method 330. The second projection method 340 is furthermore in particular different from the first projection method 330 when the rule for mapping intensity values of the image data set 400 on gray and/or color tones of the representation of the first projection data set 500 is different from the rule for mapping intensity values of the image data set 400 on gray and/or color tones of the representation of the second projection data set 510.

The first determination DET-1 of the first projection data set 500 and the second determination DET-2 of the second projection data set 510 are independent of one another and therefore it is possible both for the first determination DET-1 to be performed before the second determination DET-2 and for the second determination DET-2 to be performed before the first determination DET-1. It is also possible for the first determination DET-1 and the second determination DET-2 to take place at least partially simultaneously.

The example embodiment depicted comprises as a further optional step the first reception REC-1 of a changed display parameter via the display unit 240, wherein the changed display parameter defines a changed first projection method for the image data set 400. Herein, the first reception REC-1 is performed via the input unit 244 of the display unit 240. Herein, the user of the display unit 240 can effect a change to the representation on the output unit 245 of the display unit 240 by changing the display parameter. The changed first projection method can in particular comprise a changed first projection type, a changed first projection direction and/or a changed rule for mapping intensity values of the image data set 400 on gray and/or color tones of the representation of the changed first projection data set.

In particular, the changed first projection type of the changed first projection method can be different from the first projection type 331 of the first projection method 330. In particular, the changed first projection direction of the changed first projection method can be different from the first projection direction 332 of the first projection method. In particular, the rule for mapping intensity values of the image data set 400 on gray and/or color tones of the representation of the changed first projection data set contained in the changed first projection method can differ from the rule for mapping intensity values of the image data set 400 on gray and/or color tones of the representation of the first projection data set 510 contained in the first projection method 330.

The changed display parameter can optionally also define a changed second projection method for the image data set 400. The changed second projection method can in particular comprise a changed second projection type, a changed second projection direction and/or a changed rule for mapping intensity values of the image data set 400 on gray and/or color tones of the representation of the changed second projection data set.

The example embodiment depicted comprises as a further optional step a third determination DET-3 of a changed first projection data set by applying the changed first projection method to the image data set 400 via the display unit 240. The third determination DET-3 can in particular be performed via the computing unit 243 of the display unit 240. The third determination DET-3 can comprise all variants and developments of the first determination DET-1. If the changed display parameter comprises a changed second projection method, the third determination DET-3 can also include the determination of a changed second projection data set by applying the changed second projection method to the image data set 400 via the display unit 240, in particular via the computing unit 243 of the display unit 240.

Figure 2:
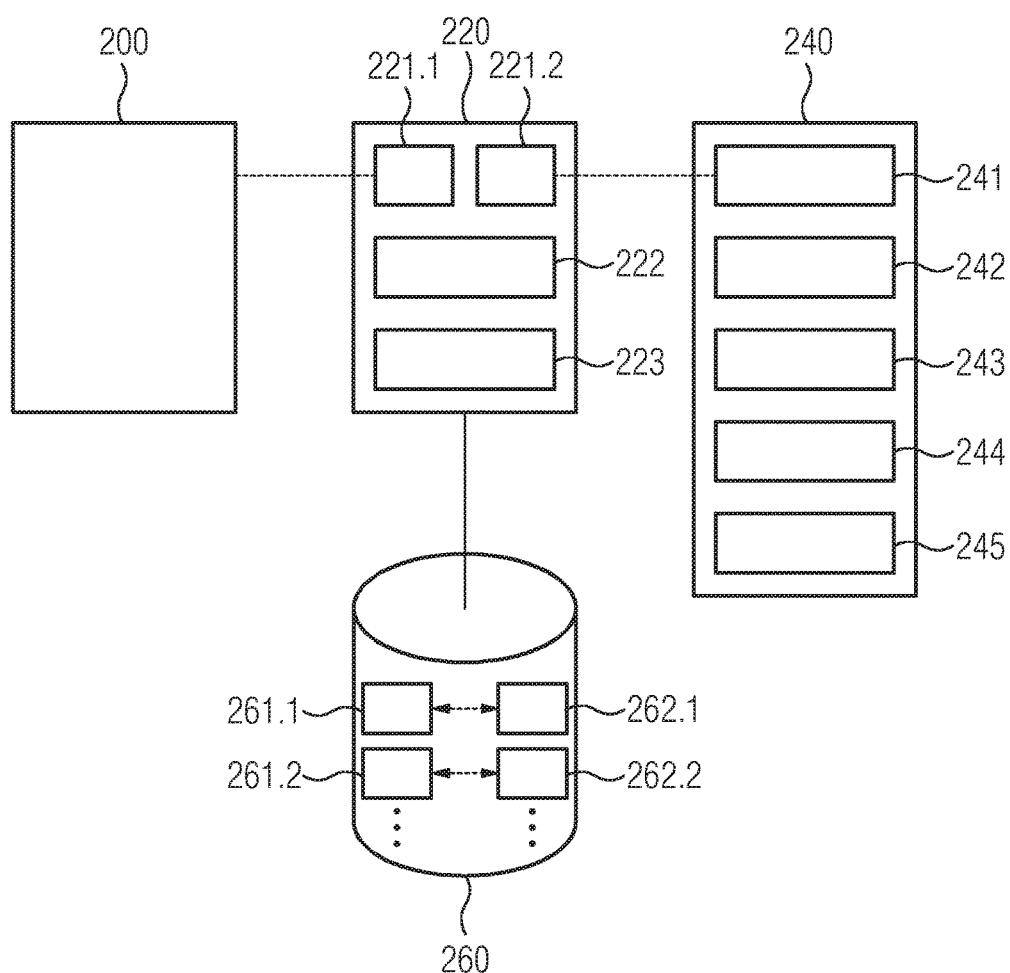
FIG. 2 shows a projection-determining system.

FIG. 2 shows a projection-determining system for the determination of a projection data set. The projection-determining system shown here is designed to carry out a method according to the invention. The projection-determining system comprises an imaging medical device 200, a reconstruction unit 220 and a display unit 240. The imaging medical device 200 can in particular be a magnetic resonance tomography system, computed tomography system or a positron emission tomography system. The reconstruction unit 220 and the display unit 240 can in particular be a computer, a microcontroller or an integrated circuit. Alternatively, the reconstruction unit 220 and/or the output unit 240 can be a real or virtual group of computers (an English technical term for a real group is "cluster", an English technical term for a virtual group is "cloud").

The reconstruction unit 220 comprises an input interface 221.1, an output interface 221.2, a computing unit 222 and a memory unit 223. The display unit 240 comprises an interface 241, a computing unit 242, a memory unit 243, an input unit 244 and an output unit 245. An input interface 221.1, an output interface 221.2 and an interface 241 can be a hardware or software interface (for example PCI, BUS, USB or FIREWIRE). A computing unit 222 of the reconstruction unit 220 and a computing unit 242 the display unit 240 can comprise hardware elements or software elements, for example a microprocessor or a so-called FPGA (English abbreviation for "field programmable gate array"). A memory unit 223 of the reconstruction unit 220 and/or a memory unit 243 of the display unit 240 can be implemented as a non-permanent working memory (random access memory, RAM for short) or as a permanent mass memory storage (hard disk, USB stick, SD card, solid state disc). An input unit 244 can in particular be implemented via a keyboard and/or a mouse. An output unit 245 can in particular be a screen. Alternatively, it can also be a printer embodied to print out image data.

In the example embodiment depicted, the reconstruction unit 220 is connected to the display unit 240 via a local area network (an English technical term, LAN for short), here in particular via an intranet. However, connection also be provided via a wide area network (an English technical term, WAN for short), for example the internet, in each case by cable or wireless means. Furthermore, a direct cable or wireless connection is possible, for example via a "universal serial bus" cable (USB cable for short) or via "Bluetooth".

In the example embodiment depicted, the reconstruction unit 220 is connected to a database 260. The connection can be embodied via a wide Area network (an English technical term, WAN for short), for example the internet, or a local area network (an English technical term, LAN for short), for example an intranet, by wired or wireless means. The database 260 can also be stored directly in the memory unit 223 the reconstruction unit. The database 260 comprises a plurality of pairs, in case consisting of a reference scan protocol 261.1, 261.2 and an assigned reference display parameter 262.1, 262.2. In the example embodiment depicted, the reference scan protocol 261.1 is assigned to the reference display parameter 262.1; the reference scan protocol 261.2 is assigned to the reference display parameter 262.2.

Figure 3:
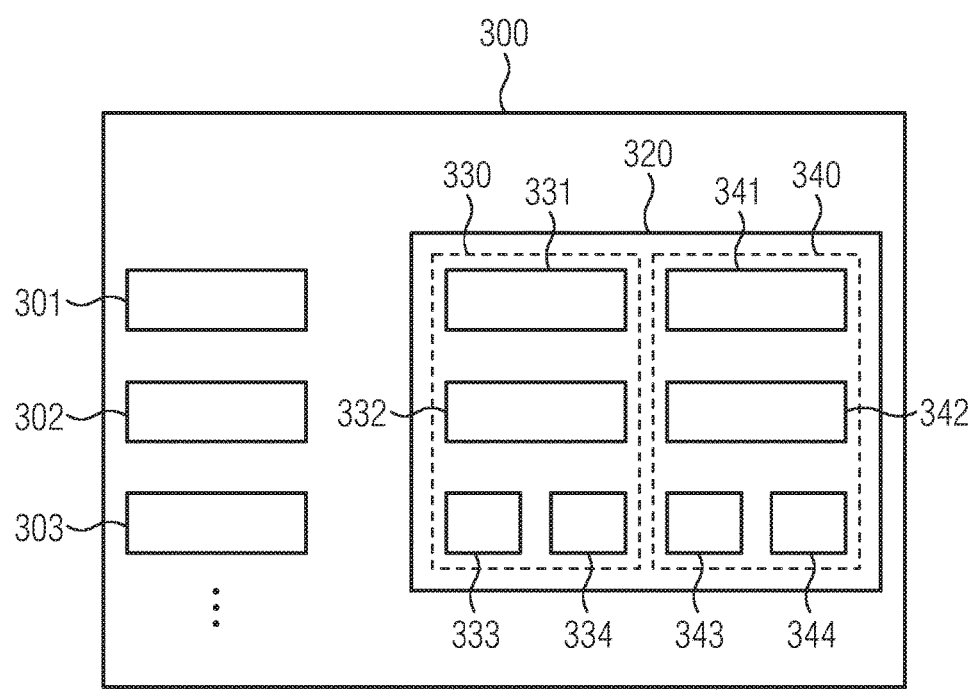
FIG. 3 shows a scan protocol comprising a display parameter.

FIG. 3 shows an example embodiment of a scan protocol 300, comprising a display parameter 320. The scan protocol 300 furthermore comprises inter alia a unique descriptor 301 of the scan protocol, a designation of the examined body part 302 and the slice thickness 303 of a tomographic acquisition. Depending upon the imaging device 200 used, the scan protocol 300 can comprise further parameters that are not depicted here. Here, the display parameter 320 comprises a first projection method 330 and a second projection method 340. The first projection method 330 comprises a first projection type 331, a first projection direction 332, a first minimum intensity value 333 to be displayed and a first maximum intensity value 334 to be displayed. The second projection method 330 comprises a second projection type 341, a second projection direction 342, a second minimum intensity value 343 to be displayed and a second maximum intensity value 344 to be displayed. Alternatively, the display parameter 320 can comprise only one first projection method 330; in addition to the first projection method 330 and the second projection method 340 the display parameter 320 can furthermore comprise further projection methods.

Herein, the first projection direction 332 is the direction with respect to which the first projection type 331 is carried out. The first minimum intensity value 333 to be displayed is shown as black in the first projection data set 500 as are all smaller intensity values. The first maximum intensity value 334 to be displayed is shown as white in the first projection data set 500 as are all larger intensity values. The gray tone of each further intensity value in the first projection data set 500 is determined by way of linear interpolation.

Herein, the second projection direction 342 is the direction with respect to which the second projection type 341 is carried out. The second minimum intensity value 333 to be depicted is shown as black in the second projection data set 510 as are all smaller intensity values. The second maximum intensity value 344 to be depicted is depicted as white in the first projection data set 510 as are all larger intensity values. The gray tone of each further intensity value in the first projection data set 510 is determined by way of linear interpolation.

Figure 4:
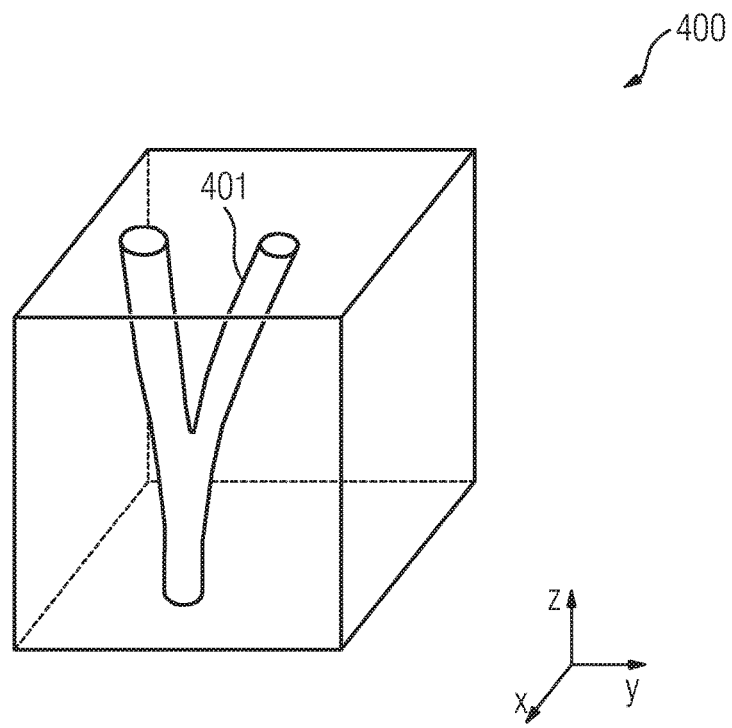
FIG. 4 shows an image data set.

FIG. 4 shows an image data set 400, which was reconstructed via a reconstruction unit 220 from a raw data set. In the example embodiment depicted, the image data set 400 is spatially three-dimensional; it comprises a vessel 401 filled with a contrast medium 401. Alternatively, it is also possible for the image data set 400 to be spatially two-dimensional. Alternatively, it is also possible for the image data set 400 to be temporally one-dimensional and spatially two-dimensional; alternatively, the image data set 400 can also be temporally one-dimensional and spatially three-dimensional. Here, the image data set 400 comprises a plurality of voxels to which an intensity value is assigned. In the example embodiment depicted, the image data set 400 forms a cuboidal volume, wherein each edge of the cuboid is parallel to a first axis X, parallel to a second axis Y or parallel to a third axis Z. Here, the first axis X, the second axis Y and the third axis Z form a right-handed Cartesian coordinate system.

Figure 5:
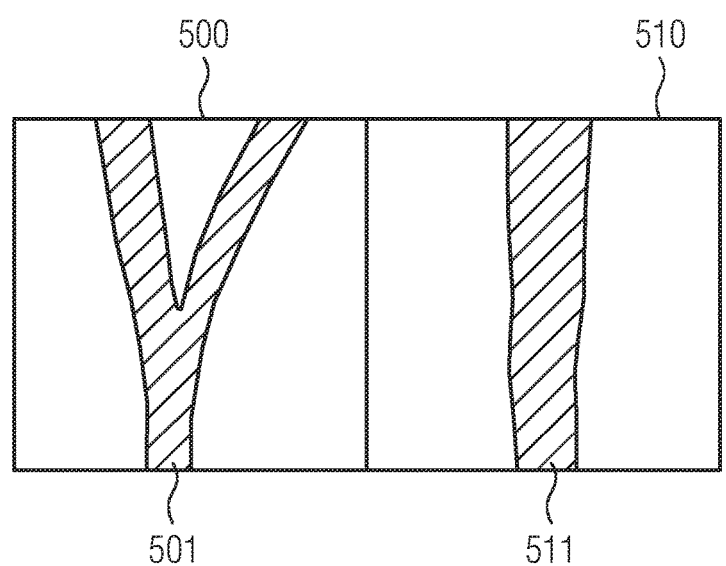
FIG. 5 shows a first projection data set and a second projection data set.

FIG. 5 shows a first projection data set 500 and a second projection data set 510, wherein the first projection data set 500 was calculated by applying a first projection method 330 to the image data set 400 via the display unit 240 and wherein the second projection data set 510 was calculated by applying a second projection method 340 to the image data set 400 via the display unit 240. The first projection data set 500 depicts a first projection 501 of the vessel 401; the second projection data set 510 depicts a second projection 502 of the vessel 400.

The first projection type 331 of the first projection method 330 and the second projection type 341 of the second projection method 340 are in each case a maximum intensity projection (MIP for short). Here, the first projection direction 332 corresponds to the first axis X; here, the second projection direction 342 corresponds to the second axis Y. In particular, therefore, the first projection method 330 is a maximum intensity projection along the first axis X; furthermore, in particular the second projection method 340 is a maximum intensity projection along the second axis Y.

The following describes by way of example possible projection types 331, 341. Herein, it is assumed that the image data set 400 is embodied as spatially three-dimensional with respect to a first axis X, a second axis Y and a third axis Z and comprises a plurality of voxels. A slice display designates a representation of all voxels with coordinates having a prespecified coordinate value with respect to precisely one of the three axes X, Y, Z. With respect to this one of the three axes X, Y, Z, these voxels have the slice thickness one and can be understood as pixels with coordinates with respect to the other two of the three axes X, Y, Z. With a slice display, the projection direction 332, 342 is defined by the precisely one of the three axes X, Y, Z.

In the case of a maximum intensity projection, the section of a bundle is considered with respect to the projection direction 332, 342 of parallel straight lines with the voxels of the image data set 400. The straight lines are arranged relative to one another such that their piercing points through a plane orthogonal to the projection direction 332, 342 form a two-dimensional point lattice. With maximum intensity projection, each of the parallel straight lines is assigned the maximum intensity value of the voxels in the image data set 400 that intersect the parallel straight line. The projection data set then corresponds then to the piercing points of the parallel straight lines through a plane orthogonal to the projection direction 332, 342, wherein the intensity value assigned to the respective straight line is assigned to each piercing point.

With multiplanar reconstruction, a specified point in the image data set 400 defines a plane orthogonal to the prespecified projection direction. The plane can in particular also intersect one, two or three of the coordinate axes X, Y, Z. Multiplanar reconstruction makes use of all voxels of the image data set 400 that have a smaller distance from the plane than a specified maximum distance. The intensity values of the contributing voxels are then projected onto the plane orthogonal to the plane. The intensity values on the plane then result, for example, from the arithmetic mean of intensity values the of projected voxels or from the maximum of the intensity values of the projected voxels.

Volume rendering can in particular be performed by tracking light beams that interact with the image data 400. Possible interactions, are for example, reflection, diffraction and scatter. Before volume rendering, the image data set 400 can be segmented, for example by threshold segmentation. Numerous methods for volume rendering are known from the prior art, for example "ray tracing" or "cinematic rendering".

With subtraction projection, a first intensity value and a second intensity value are present for each voxel in the image data set 400, wherein the second intensity value was acquired with the same imaging medical device 200 as the first intensity value and wherein the second intensity value was acquired at a time after the first intensity value. It is then possible to determine a third intensity value from the first and second intensity value of each voxel by subtraction. These third intensity values can then be projected by any type of projection onto a projection data set 500, 510.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a projection data set, comprising:
acquiring a raw data set using a scan protocol via an imaging medical device;
transmitting the raw data set and the scan protocol from the imaging medical device to a reconstruction unit;
calculating an at least two-dimensional image data set from the raw data set via the reconstruction unit;
fetching a display parameter via the reconstruction unit, the display parameter being assigned to the scan protocol, the display parameter defining a first projection method for the image data set;
transmitting the image data set and the display parameter from the reconstruction unit to a display unit, the reconstruction unit and the display unit being spatially separate; and determining a first projection data set by applying the first projection method to the image data set via the display unit.

2. The method of claim 1, wherein the scan protocol includes the display parameter, and wherein the fetching is performed by extraction of the display parameter from the scan protocol.

3. The method of claim 1, wherein the fetching is based on a database including pairs of reference scan protocols and reference display parameters, and wherein the display parameter is the reference display parameter for which an associated reference scan protocol corresponds to the scan protocol.

4. The method of claim 1, wherein the display parameter defines a second projection method for the image data set, the method further comprising:
determining a second projection data set by applying the second projection method to the image data set via the display unit.

5. The method of claim 1, further comprising:
receiving a changed display parameter via the display unit, wherein the changed display parameter defines a changed first projection method for the image data set; and
determining a changed first projection data set by applying the changed first projection method to the image data set via the display unit.

6. The method of claim 5, further comprising:
receiving a reset instruction via the display unit, and
displaying the first projection data set via the display unit.

7. The method of claim 1, wherein the image data set includes DICOM data.

8. The method of claim 1, wherein the first projection data set is a two-dimensional representation of the image data set or a temporal sequence of two-dimensional representations of the image data set.

9. The method of claim 4, wherein at least one of the first projection method and the second projection method includes at least one projection type and one projection direction.

10. The method of claim 9, wherein the projection type corresponds to one of:
slice display,
maximum intensity projection,
multiplanar reconstruction,
volume rendering, or
subtraction projection.

11. The method of claim 4, wherein at least one of the first projection method and the second projection method includes a rule for mapping intensity values of the image data set on at least one of gray and color tones of at least one of a representation of the first projection data set and a representation of the second projection data set.

12. A projection-determining system for determining a projection data set, comprising:
an imaging medical device, embodied to acquire a raw data set using a scan protocol and embodied to transmit the raw data set and the scan protocol to a reconstruction unit; and
a reconstruction unit, embodied to
calculate an at least two-dimensional image data set from the raw data set,
embodied to fetch a display parameter, the display parameter being assigned to the scan protocol and the display parameter defining a first projection method for the image data set, and
embodied to transmit the image data set nd the display parameter to a display unit; and
the display unit, spatially separate from the reconstruction unit, embodied to determine a first projection data set by applying the first projection method to the image data set.

13. A non-transitory computer-readable storage medium storing program sections, readable and executable by a projection-determining system, to carry out the method of claim 1 when the program sections are executed by the projection-determining system.

14. A non-transitory computer program product including a computer program, directly loadable into a memory of a projection-determining system, including program sections for carrying out the method of claim 1 when the program sections are executed by the projection-determining system.

15. A non-transitory computer-readable storage medium storing program sections, readable and executable by a projection-determining system, to carry out the method of claim 4 when the program sections are executed by the projection-determining system.

16. The method of claim 2, wherein the fetching is based on a database including pairs of reference scan protocols and reference display parameters, and wherein the display parameter is the reference display parameter for which an associated reference scan protocol corresponds to the scan protocol.

17. The method of claim 2, wherein the display parameter furthermore defines a second projection method for the image data set, the method further comprising:
determining a second projection data set by applying the second projection method to the image data set via the display unit.

18. The method of claim 2, further comprising:
receiving a changed display parameter via the display unit, wherein the changed display parameter defines a changed first projection method for the image data set; and
determining a changed first projection data set by applying the changed first projection method to the image data set via the display unit.

19. The method of claim 18, further comprising:
receiving a reset instruction via the display unit, and
displaying the first projection data set via the display unit.

20. The method of claim 1, wherein at least one of the first projection method and a second projection method includes at least one projection type and one projection direction.

21. The method of claim 20, wherein the projection type corresponds to one of:
slice display,
maximum intensity projection,
multiplanar reconstruction,
volume rendering, or
subtraction projection.

22. A non-transitory computer program product including a computer program, directly loadable into a memory of a projection-determining system, including program sections for carrying out the method of claim 4 when the program sections are executed by the projection-determining system.

23. The method of claim 1, wherein the scan protocol comprises parameters set for acquisition of the raw data set at the medical imaging device.

* * * * *